United States Patent [19]

Myers, Jr. et al.

[11] 4,107,198

[45] Aug. 15, 1978

[54] CATALYTIC CODIMERIZATION OF NORBORNADIENE WITH ACRYLONITRILE

[75] Inventors: Harry K. Myers, Jr., Aston; Abraham Schneider, Overbrook Hills, both of Pa.

[73] Assignee: Sun Oil Company of Pennsylvania, Philadelphia, Pa.

[21] Appl. No.: 812,208

[22] Filed: Jul. 1, 1977

[51] Int. Cl.$^2$ .................. C07C 120/00; C07C 121/46
[52] U.S. Cl. .................................................. 260/464
[58] Field of Search .......................................... 260/464

[56] References Cited

U.S. PATENT DOCUMENTS

| | | | |
|---|---|---|---|
| 2,875,256 | 2/1959 | Hyman et al. | 260/666 R |
| 2,940,984 | 6/1960 | Applequist et al. | 260/464 X |
| 3,271,438 | 9/1966 | Cannell | 260/464 |
| 3,340,290 | 9/1967 | Blanchard | 260/464 |
| 3,641,175 | 2/1972 | Wilke et al. | 260/666 B |
| 3,956,355 | 5/1976 | Ueshima | 260/464 |

OTHER PUBLICATIONS

Noyori, et al., J.A.C.S., 97:4 (2-19-75) pp. 812-820.

*Primary Examiner*—Joseph Paul Brust
*Attorney, Agent, or Firm*—J. Edward Hess; Donald R. Johnson; Anthony Potts, Jr.

[57] ABSTRACT

Norbornadiene and acrylonitrile are catalytically codimerized in the presence of a three-component homogeneous catalytic system consisting of nickel acetylacetonate, triphenylphosphine and an alkyl aluminum chloride. The codimer can be used as a precursor for missile fuel.

10 Claims, No Drawings

CATALYTIC CODIMERIZATION OF NORBORNADIENE WITH ACRYLONITRILE

BACKGROUND OF THE INVENTION

The invention herein described was made in the course of or under a contract thereunder with the United States Air Force Systems Command.

The invention relates to the catalytic codimerization of norbornadiene, hereinafter referred to as NBD, and acrylonitrile, hereinafter referred to as AN. Particularly, the invention relates to the preparation of a codimer using a specified catalyst system.

The codimer can be used as a precursor for a missile fuel. The codimer contains a nitrile which can be hydrolyzed to an acid which can be decarboxylated. The resulting decarboxylated hydrocarbon can be used as a missile fuel.

NBD is also known as bicyclo-(2.2.1) heptadiene-2,5. A method of preparation is disclosed in U.S. Pat. No. 2,875,256 issued Feb. 24, 1959. The latter can be represented by either one of the following structural formulas:

 OR 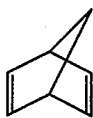

(I)   (I)

NBD can be easily dimerized to a exo-exo hexacyclic dimer. Thus one problem in reacting NBD with another hydrocarbon reactant is to minimize the formation of the foregoing dimer while encouraging the formation of the desired codimer.

In the Journal of the American Chemical Society /97:4/ Feb. 19, 1975, pages 812 & ff, R. Noyori et al in an article titled "Nickel (O)-Catalyzed Reaction of Quadricyclane with Electron-Deficient Olefins" discloses the reaction of NBD and AN using bis(acrylonitrile)nickel(O). The resulting codimer product has the following structure:

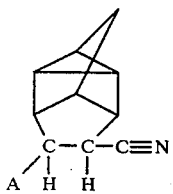 OR 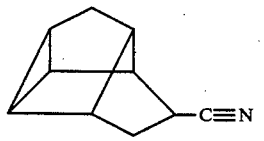

(II)   (II)

The reaction was run at a temperature of 40° C for a substantial amount of time. Yet the yield of codimer II was low.

Thus, as the aforementioned work indicates, the specific problem is to obtain codimer II in both a high conversion and selectivity and with a rapid reaction rate.

SUMMARY OF THE INVENTION

Rapid codimerization of NBD and AN is obtained using a catalytic amount of a three-component homogeneous catalytic system consisting of nickel acetylacetonate, triphenylphosphine ($(C_6H_5)_3P$), and an alkyl aluminum chloride. The nickel compound can be the hydrate ($2H_2O$) or be the anhydrous form. Both the yield and selectivity as to codimer II are excellent and the reaction rate is relatively rapid. Resulting codimer can be a precursor to a missile fuel.

DESCRIPTION

The nickel acetylacetonate, is hereinafter referred to as $NiA_2$; the triphenylphosphine as TPP and the alkyl aluminum chloride as AAC.

The catalytic codimerization of NBD and AN via present invention can be represented by the following formula reaction:

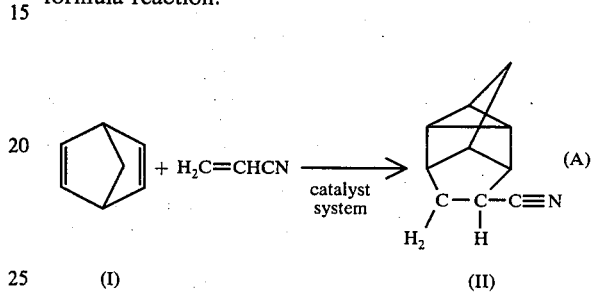

As shown NBD and AN are contacted in the presence of the catalyst system defined herein. Codimer II is a tetracyclic nitrile having the molecular formula $C_{10}H_{11}N$.

The NBD used can contain a nominal amount of similar hydrocarbons, however, which if present should not be of a type which could adversely effect the reaction. If the NBD used contains such an undesirable hydrocarbon it can be removed by known means. The foregoing also applies to the AN used. Thus, the reactants used in the invention can consist essentially of NBD and AN.

In the codimerization of NBD and AN 1 mole of each reacts with the other to form 1 mole of the NBD-AN codimer II. However, if the NBD to AN mole ratio is too large, homodimerization can occur with its adverse effect on yields. On the other hand if the NBD to AN mole ratio is too low then the yield per pass can be too low and hence, uneconomical. Within the aforementioned limits a preferred NBD to AN mole ratio is in the range between from about 0.1 to about 20 with about 0.2 to about 5 more preferred.

The catalytic system favoring the aforementioned codimerization reaction (A) contains three components. All three components of the catalyst system are commercially available and methods for their preparation are reported in the literature. The three are $NiA_2$, TPP and AAC. The AAC can be selected from the group consisting of diethylaluminum chloride, ethyl aluminum dichloride and ethyl aluminum sesquichloride. The latter three are hereinafter referred to as DEAC, EADC and EASC, respectively. The amount of the system present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system.

The amount of NBD present compared to the $NiA_2$ is catalytically sufficient to obtain the desired product.

Generally, the NBD to $NiA_2$ mole ratio can range between from about 10 to about 2000 with a preferred range between from about 20 to about 1000.

The second component of the catalyst system is TPP which has the following formula: $(C_6H_5)_3P$. The amount of this second component of the catalyst system should be catalytically sufficient to obtain the desired product. The amount of the second component can vary substantially but generally it is related to the amount of $NiA_2$ present. An operable TPP to $NiA_2$ mole ratio can range between from about 0.1 to about 100 with 0.25 to about 20 more preferred.

DEAC, EADC or EASC is the third component of the catalyst system with DEAC preferred. The amount of the third component can vary substantially but generally it relates to the amount of $NiA_2$ used. An effective DEAC, EADC or EASC to $NiA_2$ mole ratio can be between from about 1 to about 100 with from about 3 to about 50 preferred and from about 5 to about 20 more preferred. Excess DEAC, EADC or EASC also serves as a scavenger. Generally, however, when DEAC, EADC or EASC is used it is advantageous to conduct the reaction under substantially anhydrous conditions and under an inert gas blanket.

Selectivity refers to the amount of a particular compound formed divided by the amount of all compounds formed. From a commercial standpoint economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is, the feed and the components of the catalyst, and thereby provide for a homogeneous reaction medium. Some solvent can be added to the system as a carrier for one or more of the catalyst components. For example, DEAC is often maintained in a solvent such as toluene. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, cycloolefins, ethers, halogenated aromatics, halogenated paraffins and halogenated cycloparaffins. Specific examples include benzene, toluene, xylenes, cyclohexane, cyclopentene, diethylether, chlorobenzene, bromobenzene, chlorinated cyclohexane and the like. As to the amount of solvent used, excessive amounts decrease the reaction rate, and thus, adversely affect the economics for a commercial operation.

The codimerization of NBD and AN with the three-component catalyst system can occur at ambient temperature. Thus, the temperature of the homogeneous feed catalyst system mixture need not be raised to initiate reaction (A). If the mixture is at an extremely low temperature, then heating of the mixture could be necessary. If the temperature increases too much then some cooling would be required. Generally, however, the codimerization of NBD and AN with the three-component catalyst system is not characterized by an extremely rapid exotherm when a reasonable amount of catalyst is used.

Selective codimerization of the NBD and AN occurs in a liquid phase, therefore it is not desirable to have the reaction temperature largely exceed the boiling points of the NBD and/or any solvent. Conversely, if the temperature is too low the reaction rate would be too low to be economically feasible. An operable temperature range is between from about $-20°$ C to about $100°$ C with about $25°$ C to about $85°$ C a preferred range. The operating pressure can vary substantially, however, it can range from about atmospheric up to about 2000 psi with 1000 psi a preferred upper value. Process economics favor lower operating pressure, however, a moderately elevated reaction pressure may be desirable to keep the AN in solution.

To further illustrate the invention, the following examples and comparisons are provided.

EXAMPLES

Into a glass reaction vessel were added 0.033 millimoles of $NiA_2$ hydrate and 0.168 millimoles of TPP (0.12 molar in benzene) all at $24°$ C and then deaerated. Then 4.93 millimoles of NBD were added and the mixture was warmed to $53°$ C and then cooled to $33°$. To the vessel were then added 0.70 millimoles of DEAC (1 molar in benzene). Then 14.8 millimoles of AN were added to the vessel. After 456 minutes the reaction mixture was quenched and a catalyst-free sample of product analyzed by vapor phase chromatographic analysis (vpc). The analysis indicated that 53.7 wt. % of the NBD was converted with an 85.5% selectivity to codimer II. Also the vpc indicated that about 34.7% of the AN was converted with about a 44% selectivity to codimer II. The total product yield was about 45.9 wt. %. A run using just $NiA_2$ and DEAC failed to yield codimer II.

Comparative runs were made using the following catalyst systems: cobaltic acetylacetonate and DEAC and TPP; $CoA_3$, DEAC and 1,2 bisdiphenylphosphino ethane; ferric acetylacetonate, DEAC and TPP; and rhodium acetylacetonate, DEAC and TPP. The first two catalyst systems yielded Binor-S as the major product. The next two catalyst systems yielded no major codimer product.

The invention claimed is:

1. Process for the catalytic codimerization of norbornadiene with acrylonitrile comprising:
    (a) contacting norbornadiene and acrylonitrile in the presence of a catalytic amount of a three-component homogeneous catalytic system consisting of nickel acetylacetonate, triphenylphosphine and an alkyl aluminum chloride selected from the group consisting of diethylaluminum chloride, ethyl aluminum dichloride and ethyl aluminum sesquichloride;
    (b) having the contacting occurring at a temperature within the range between from about $-20°$ C to about $100°$ C; and
    (c) continuing the contacting until a norbornadiene-acrylonitrile codimer having the following structure

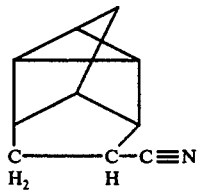

is prepared.

2. Process according to claim 1 wherein the triphenylphosphine to the acetylacetonate mole ratio is in the range between from about 0.1 to about 100.

3. Process according to claim 1 wherein the norbornadiene to acrylonitrile mole ratio is in the range between from about 0.1 to about 20.

4. Process according to claim 1 wherein the norbornadiene to the acetylacetonate mole ratio is in the range between from about 10 to about 2000.

5. Process according to claim 1 wherein the alkyl aluminum chloride to the acetylacetonate mole ratio is in the range between from about 1 to about 100.

6. Process according to claim 5 wherein an inert solvent is present.

7. Process according to claim 6 wherein the inert solvent is selected from the group consisting of aromatic hydrocarbon, cycloparaffin, cycloolefin, ether, halogenated aromatic, halogenated paraffin and halogenated cycloparaffin.

8. Process according to claim 7 wherein the triphenylphosphine to the acetylacetonate mole ratio is in the range between from about 0.1 to about 100.

9. Process according to claim 8 wherein the alkyl aluminum chloride to the acetylacetonate mole ratio is in the range between from about 1 to about 100.

10. Process according to claim 9 wherein the norbornadiene to the acrylonitrile mole ratio is in the range between from about 0.1 to about 20.

* * * * *